(12) United States Patent
Baehner et al.

(10) Patent No.: US 8,883,976 B2
(45) Date of Patent: *Nov. 11, 2014

(54) ANTIBODIES AGAINST HUMAN TWEAK AND USES THEREOF

(75) Inventors: Monika Baehner, Munich (DE); Hendrik Knoetgen, Penzberg (DE); Jens Niewoehner, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 417 days.

This patent is subject to a terminal disclaimer.

(21) Appl. No.: 13/427,951

(22) Filed: Mar. 23, 2012

(65) Prior Publication Data

US 2012/0207750 A1    Aug. 16, 2012

Related U.S. Application Data

(62) Division of application No. 13/287,256, filed on Nov. 2, 2011, which is a division of application No. 12/748,487, filed on Mar. 29, 2010, now Pat. No. 8,093,006.

(30) Foreign Application Priority Data

Apr. 2, 2009   (EP) .................................... 09004905

(51) Int. Cl.
*C07K 16/00* (2006.01)
*C07K 16/28* (2006.01)
*A61K 39/00* (2006.01)

(52) U.S. Cl.
CPC ......... *C07K 16/2875* (2013.01); *C07K 2317/24* (2013.01); *C07K 2317/56* (2013.01); *C07K 2317/92* (2013.01); *A61K 2039/505* (2013.01); *C07K 2317/565* (2013.01); *C07K 2317/21* (2013.01)
USPC .................................. 530/387.1; 530/388.24

(58) Field of Classification Search
None
See application file for complete search history.

(56) References Cited

U.S. PATENT DOCUMENTS

| | | | |
|---|---|---|---|
| 6,207,642 B1 | 3/2001 | Wiley et al. | |
| 6,824,773 B2 | 11/2004 | Wiley et al. | |
| 6,943,146 B2 | 9/2005 | Jakubowski et al. | |
| 7,087,725 B2 | 8/2006 | Browning et al. | |
| 7,109,298 B2 | 9/2006 | Browning et al. | |
| 7,129,061 B1 | 10/2006 | Browning et al. | |
| 7,169,387 B2 | 1/2007 | Rennert et al. | |
| 8,093,006 B2 * | 1/2012 | Baehner et al. | ................ 435/7.1 |
| 2004/0033225 A1 | 2/2004 | Browning et al. | |
| 2005/0008636 A1 | 1/2005 | Rennert et al. | |
| 2005/0112666 A1 | 5/2005 | Browning et al. | |
| 2006/0240004 A1 | 10/2006 | Burkly et al. | |
| 2007/0110745 A1 | 5/2007 | Rennert et al. | |
| 2007/0280940 A1 | 12/2007 | Winkles et al. | |
| 2008/0171037 A1 | 7/2008 | Ashkenazi et al. | |
| 2008/0187544 A1 | 8/2008 | Burkly et al. | |
| 2008/0213837 A1 | 9/2008 | Ashkenazi et al. | |
| 2008/0241163 A1 | 10/2008 | Burkly et al. | |
| 2008/0279853 A1 | 11/2008 | Burkly et al. | |
| 2008/0286271 A1 | 11/2008 | Ashkenazi et al. | |
| 2009/0068102 A1 | 3/2009 | Burkly et al. | |
| 2009/0124993 A1 | 5/2009 | Burkly et al. | |
| 2012/0083015 A1 * | 4/2012 | Baehner et al. | ............. 435/69.7 |

FOREIGN PATENT DOCUMENTS

| | | |
|---|---|---|
| WO | 98/05783 | 2/1998 |
| WO | 98/35061 | 8/1998 |
| WO | 00/42073 | 7/2000 |
| WO | 01/22187 | 3/2001 |
| WO | 01/30429 | 5/2001 |
| WO | 03/086311 | 10/2003 |
| WO | 2006/130374 | 5/2006 |
| WO | 2006/088890 | 8/2006 |
| WO | 2006/089095 | 8/2006 |
| WO | 2006/052926 | 9/2006 |
| WO | 2006/096487 | 9/2006 |

OTHER PUBLICATIONS

The extened European Search Report, issued on Apr. 25, 2013, in the related European Patent Application No. 13153217.8., pp. 10.
The Russian Office Action, issued on Feb. 13, 2014, in the related Russian application No. 2011143903.
Roitt et al., Immunology—translation from English—Moscow: Mir, 2000, p. 110.
Rudikoff et al., Proc. Natl. Acad. Sci. USA, Immunology, vol. 79, (1982), pp. 1979-1983.
Kang et al., Proc. Natl. Acad. Sci. USA, vol. 88, (1991), pp. 11120-11123.
Jakubowski et al., "Journal of Cell Science" 115(2):267-274 ( 2002).
Chicheportiche et al., "J. Biol. Chem." 272(51):32401-32410 ( 1997).
Winkles et al., "Frontiers in Bioscience" 12:2761-2771 ( 2007).
"International Search Report for EP09004905.7—Sep. 14, 2009".
Campbell et al., "J. Immunol." 176:1889-1898 ( 2006).
Lynch et al., "J. Biol. Chem." 274:8455-8459 ( 1999).
Nakayama et al., "Biochem. Biophys. Res. Comm." 306:819-825 ( 2003).
Masters et al., "Curr. Biol." 8:525 ( 1998).
Chicheportiche et al., "Arthritis Research" 4(2):126-133 ( 2001).
Desplat-Jego et al., "Clinical Immunology" 117(1):15-23 ( 2005).

\* cited by examiner

*Primary Examiner* — Maher Haddad

(57) ABSTRACT

An antibody binding to TWEAK comprising as heavy chain variable domain a CDR3H selected from the group consisting of SEQ ID NO: 8, 16 or 24.

4 Claims, 2 Drawing Sheets

ANTIBODIES AGAINST HUMAN TWEAK AND USES THEREOF

PRIORITY TO RELATED APPLICATION(S)

This application is a division of U.S. application Ser. No. 13/287,256, filed Nov. 2, 2011, now allowed; which is a division of U.S. application Ser. No. 12/748,487, filed Mar. 29, 2010, now U.S. Pat. No. 8,093,006, issued Jan. 10, 2012; which claims the benefit of European Patent Application No. 09004905.7, filed Apr. 2, 2009. The entire contents of the above-identified applications are hereby incorporated by reference.

SEQUENCE LISTING

The instant application contains a Sequence Listing. An ASCII copy, created on Feb. 23, 2010, is named 26044.txt, is 87,526 bytes in size, and was submitted in parent U.S. application Ser. No. 12/748,487.

FIELD OF THE INVENTION

The present invention relates to antibodies against human TWEAK (TWEAK antibodies), methods for their production, pharmaceutical compositions containing said antibodies, and uses thereof.

BACKGROUND OF THE INVENTION

Human TWEAK (UniProtKB O43508, TNF-related weak inducer of apoptosis) is a cell surface associated type II transmembrane protein. TWEAK is described in Chicheportiche, Y. et al., J. Biol. Chem. 272 (1997) 32401-32410; Marsters, S. A. et al., Curr. Biol. 8 (1998) 525-528; Lynch, C. N et al., J. Biol. Chem. 274 (1999) 8455-8459. The active form of TWEAK is a soluble homotrimer. Human and murine TWEAK show 93% sequence identity in receptor binding domain. The TWEAK receptor Fn14 (fibroblast growth factor inducible 14 kDa protein) is a 129 aa type I transmembrane protein consisting of one single cystein rich domain in ligand binding domain. Signaling of TWEAK occurs via NF-KB pathway activation. TWEAK mRNA is expressed in a variety of tissues and found in most major organs like heart, brain, skeletal muscle, and pancreas, tissues related to the immune system like spleen, lymph nodes, and thymus. Fn14 mRNA has been detected in heart, brain, lung, placenta, vascular EC and smooth muscle cells. TWEAK-null and Fn14-null knockout mice are viable, healthy and fertile and have more natural killer cells and display an enhanced innate inflammatory response. TWEAK is involved in apoptosis, proliferation, angiogenesis, ischemic penumbra, cerebral edema, multiple sclerosis.

Anti-TWEAK antibodies are mentioned in WO 1998/005783, WO 2000/042073, WO 2003/086311, WO 2006/130429, WO 2006/130374, WO 2006/122187, WO 2006/089095, WO 2006/088890, WO 2006/052926.

SUMMARY OF THE INVENTION

The invention includes an isolated antibody binding to human TWEAK, characterized in comprising as heavy chain variable domain CDR3 region (CDR3H) selected from the group consisting of the amino acid sequence of SEQ ID NO: 8, 16 or 24. Preferably, the antibody is a chimeric, humanized or T-cell epitope depleted antibody.

The invention includes an isolated antibody comprising a variable light chain with the amino acid sequence of SEQ ID NO:1 and a variable heavy chain with the amino acid sequence of SEQ ID NO:5; or a variable light chain with the amino acid sequence of SEQ ID NO:9 and a variable heavy chain with the amino acid sequence of SEQ ID NO:13; or a variable light chain with the amino acid sequence of SEQ ID NO:17 and a variable heavy chain with the amino acid sequence of SEQ ID NO:21.

A preferred antibody according to the invention comprises CDR1H with the amino acid sequence of SEQ ID NO:6, CDR2H with the amino acid sequence of SEQ ID NO:7, and CDR3H with the amino acid sequence of SEQ ID NO:8.

Another preferred antibody according to the invention comprises CDR1H with the amino acid sequence of SEQ ID NO:14, CDR2H with the amino acid sequence of SEQ ID NO:15, and CDR3H with the amino acid sequence of SEQ ID NO:16.

Another preferred antibody according to the invention comprises CDR1H with the amino acid sequence of SEQ ID NO:22, CDR2H with the amino acid sequence of SEQ ID NO:23, and CDR3H with the amino acid sequence of SEQ ID NO:24.

Another preferred antibody according to the invention comprises CDR1H with the amino acid sequence of SEQ ID NO:22, CDR2H with the amino acid sequence of SEQ ID NO:74, and CDR3H with the amino acid sequence of SEQ ID NO:24.

Another preferred antibody according to the invention comprises CDR1H with the amino acid sequence of SEQ ID NO:22, CDR2H with the amino acid sequence of SEQ ID NO:75, and CDR3H with the amino acid sequence of SEQ ID NO:24.

Another preferred antibody according to the invention comprises CDR1H with the amino acid sequence of SEQ ID NO:6, CDR2H with the amino acid sequence of SEQ ID NO:7, CDR3H with the amino acid sequence of SEQ ID NO:8, CDR1L with the amino acid sequence of SEQ ID NO:2, CDR2L with the amino acid sequence of SEQ ID NO:3, and CDR3L with the amino acid sequence of SEQ ID NO:4.

Another preferred antibody according to the invention comprises CDR1H with the amino acid sequence of SEQ ID NO:14, CDR2H with the amino acid sequence of SEQ ID NO:15, CDR3H with the amino acid sequence of SEQ ID NO:16, CDR1L with the amino acid sequence of SEQ ID NO:10, CDR2L with the amino acid sequence of SEQ ID NO:11, and CDR3L with the amino acid sequence of SEQ ID NO:12.

Another preferred antibody according to the invention comprises CDR1H with the amino acid sequence of SEQ ID NO:22, CDR2H with the amino acid sequence of SEQ ID NO:23, CDR3H with the amino acid sequence of SEQ ID NO:24, CDR1L with the amino acid sequence of SEQ ID NO:18, CDR2L with the amino acid sequence of SEQ ID NO:19, and CDR3L with the amino acid sequence of SEQ ID NO:20.

Another preferred antibody according to the invention comprises CDR1H with the amino acid sequence of SEQ ID NO:22, CDR2H with the amino acid sequence of SEQ ID NO:74, CDR3H with the amino acid sequence of SEQ ID NO:24, CDR1L with the amino acid sequence of SEQ ID NO:18, CDR2L with the amino acid sequence of SEQ ID NO:19, and CDR3L with the amino acid sequence of SEQ ID NO:20.

Another preferred antibody according to the invention comprises CDR1H with the amino acid sequence of SEQ ID NO:22, CDR2H with the amino acid sequence of SEQ ID NO:75, CDR3H with the amino acid sequence of SEQ ID NO:24, CDR1L with the amino acid sequence of SEQ ID NO:18, CDR2L with the amino acid sequence of SEQ ID NO:19, and CDR3L with the amino acid sequence of SEQ ID NO:20.

Preferably the antibody of the invention comprises as light chain variable domain an amino acid sequence selected of the group consisting of SEQ ID NO:1, 9, 17, 32, 33, 34, 35, 44, 45, 46, 47, 55, 56, 57, 58, 59, or 60.

Preferably the antibody of the invention comprises as heavy chain variable domain an amino acid sequence selected from the group consisting of SEQ ID NO:5, 13, 21, 36, 37, 38, 39, 40, 41, 42, 43, 48, 49, 50, 51, 52, 53, 54, 61, 62, 63, 64, 65, 66, 67, 68, 69, 70, 71, 72, or 73.

A preferred antibody comprises as light chain variable domain an amino acid sequence selected from the group consisting of SEQ ID NO: 1, 32, 33, 34, 35 and as heavy chain variable domain an amino acid sequence selected from the group consisting of SEQ ID NO:5, 36, 37, 38, 39, 40, 41, 42, and 43.

Another preferred antibody comprises as light chain variable domain an amino acid sequence selected from the group consisting of SEQ ID NO:9, 44, 45, 46, 47 and as heavy chain variable domain an amino acid sequence selected from the group consisting of SEQ ID NO:13, 48, 49, 50, 51, 52, 53, and 54.

Another preferred antibody comprises as light chain variable domain an amino acid sequence selected from the group consisting of SEQ ID NO:17, 55, 56, 57, 58, 59, and 60 and as heavy chain variable domain an amino acid sequence selected from the group consisting of SEQ ID NO:21, 61, 62, 63, 64, 65, 66, 67, 68, 69, 70, 71, 72, and 73.

Preferred antibodies comprise light and heavy variable chain amino acid sequence combinations selected from the group consisting of the following amino acid sequences: SEQ ID NO: 1/5, 1/36, 1/37, 1/38 1/39, 1/40, 1/41, 1/42, 1/43, 32/5, 32/36, 32/37, 32/38, 32/39, 32/40, 32/41, 32/42, 32/43, 33/5, 33/36, 33/37, 33/38, 33/39, 33/40, 33/41, 33/42, 33/43, 34/5, 34/36, 34/37, 34/38 34/39, 34/40, 34/41, 34/42, 34/43, 35/5, 35/36, 35/37, 35/38, 35/39, 35/40, 35/41, 35/42, 35/43; 9/13, 9/48, 9/49; 9/50, 9/51, 9/52, 9/53, 9/54, 44/13, 44/48, 44/49; 44/50, 44/51, 44/52, 44/53, 44/54, 45/13, 45/48, 45/49; 45/50, 45/51, 45/52, 45/53, 45/54, 46/13, 46/48, 46/49; 46/50, 46/51, 46/52, 46/53, 46/54, 47/13, 47/48, 47/49; 47/50, 47/51, 47/52, 47/53, 47/54; 17/21, 17/61, 17/62, 17/63, 17/64, 17/65, 17/66, 17/67, 17/68, 17/69, 17/70, 17/71, 17/72, 17/73, 55/21, 55/61, 55/62, 55/63, 55/64, 55/65, 55/66, 55/67, 55/68, 55/69, 55/70, 55/71, 55/72, 55/73, 56/21, 56/61, 56/62, 56/63, 56/64, 56/65, 56/66, 56/67, 56/68, 56/69, 56/70, 56/71, 56/72, 56/73, 57/21, 57/61, 57/62, 57/63, 57/64, 57/65, 57/66, 57/67, 57/68, 57/69, 57/70, 57/71, 57/72, 57/73, 58/21, 58/61, 58/62, 58/63, 58/64, 58/65, 58/66, 58/67, 58/68, 58/69, 58/70, 58/71, 58/72, 58/73, 59/21, 59/61, 59/62, 59/63, 59/64, 59/65, 59/66, 59/67, 59/68, 59/69, 59/70, 59/71, 59/72, 59/73, 60/21, 60/61, 60/62, 60/63, 60/64, 60/65, 60/66, 60/67, 60/68, 60/69, 60/70, 60/71, 60/72, 60/73 (wherein 47/52 means an antibody comprising variable light chain amino acid sequence of SEQ ID NO: 47 and variable heavy chain amino acid sequence SEQ ID NO: 52).

Another preferred antibody according to the invention comprises a variable chain amino acid sequence combination selected from the group consisting of light and heavy variable chains with amino acid sequences of SEQ ID NO:57 and SEQ ID NO:68; SEQ ID NO:57 and SEQ ID NO:69; SEQ ID NO:57 and SEQ ID NO:70; SEQ ID NO:57 and SEQ ID NO:71; SEQ ID NO:57 and SEQ ID NO:72; SEQ ID NO:57 and SEQ ID NO:73; SEQ ID NO:58 and SEQ ID NO:68; SEQ ID NO:58 and SEQ ID NO:69; SEQ ID NO:58 and SEQ ID NO:70; SEQ ID NO:58 and SEQ ID NO:71; SEQ ID NO:58 and SEQ ID NO:72; and SEQ ID NO:58 and SEQ ID NO:73.

A further embodiment of the invention is an antibody having a variable heavy chain or light chain selected from the group consisting of variable heavy or light chains with amino acid sequences of SEQ ID NO: 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 and 73. Such a variable heavy chain or light chain is useful as intermediate for the generation of an antibody according to the invention.

Preferably the antibody binding to TWEAK and being characterized by the above mentioned amino acid sequences and amino acid sequence fragments is of human IgG1 isotype.

An antibody according to the invention shows a half-life of a complex between soluble human TWEAK (amino acids 99-249) and antibody of 53 minutes or lower (preferably 20 minutes and lower and especially preferred between 10 and 20 minutes) at 25° C., measured by Biacore. Anti-TWEAK antibodies showing such low half-life are especially preferred for use in the treatment of tumor diseases.

An antibody according to the invention specifically binds to human TWEAK and inhibits the interaction between human TWEAK and Fn14 with an $IC_{50}$ value of 15 ng/ml or lower. The antibody is preferably of human IgG1 isotype. Preferably the antibody is a humanized or human antibody. As used herein, $IC_{50}$ means the amount of antibody that blocks 50% of the interaction between human TWEAK and Fn14.

An antibody according to the invention preferably shows a half-life of a complex between soluble murine TWEAK (amino acids 81-225) and antibody of 70 minutes or lower (preferably between 40 and 70 minutes) at 25° C., measured by Biacore and binds to murine TWEAK and inhibits the interaction between murine TWEAK and Fn14 with an $IC_{50}$ value of 40 ng/ml or lower.

A further embodiment of the invention is a pharmaceutical composition comprising an antibody according to the invention.

A further embodiment of the invention is the use of an antibody according to the invention for the manufacture of a pharmaceutical composition.

A further embodiment of the invention is the use of an antibody according to the invention for the treatment of cancer, preferably of colon, lung or pancreatic cancer.

A further embodiment of the invention is a method for the manufacture of a pharmaceutical composition comprising an antibody according to the invention.

A further embodiment of the invention is a nucleic acid encoding a heavy chain variable domain and/or a light chain variable domain of an antibody according to the invention.

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

Antibodies according to the invention show benefits for patients in need of a TWEAK targeting therapy. The antibodies according to the invention have new and inventive properties causing a benefit for a patient suffering from a tumor disease, especially suffering from colon, lung, or pancreatic cancer.

The invention further provides a method for treating a patient suffering from cancer, especially from colon, lung, or pancreatic cancer, comprising administering to a patient diagnosed as having such a disease (and therefore being in need of such a therapy) an effective amount of an antibody binding to TWEAK according to the invention. The antibody is administered preferably in a pharmaceutical composition.

A further embodiment of the invention is a method for the treatment of a patient suffering from cancer, especially from colon, lung, or pancreatic cancer, characterized by administering to the patient an antibody according to the invention.

The invention further includes the use of an antibody according to the invention for the treatment of a patient suffering from cancer, especially from colon, lung, or pancreatic cancer, and for the manufacture of a pharmaceutical composition according to the invention. In addition, the invention comprises a method for the manufacture of a pharmaceutical composition according to the invention.

The invention also includes a pharmaceutical composition comprising an antibody according to the invention, optionally together with a buffer and/or an adjuvant useful for the formulation of antibodies for pharmaceutical purposes.

The invention further provides a pharmaceutical composition comprising an antibody according to the invention in a pharmaceutically acceptable carrier. In one embodiment, the pharmaceutical composition may be included in an article of manufacture or kit.

DETAILED DESCRIPTION OF THE EMBODIMENTS OF THE INVENTION

Figure 1:
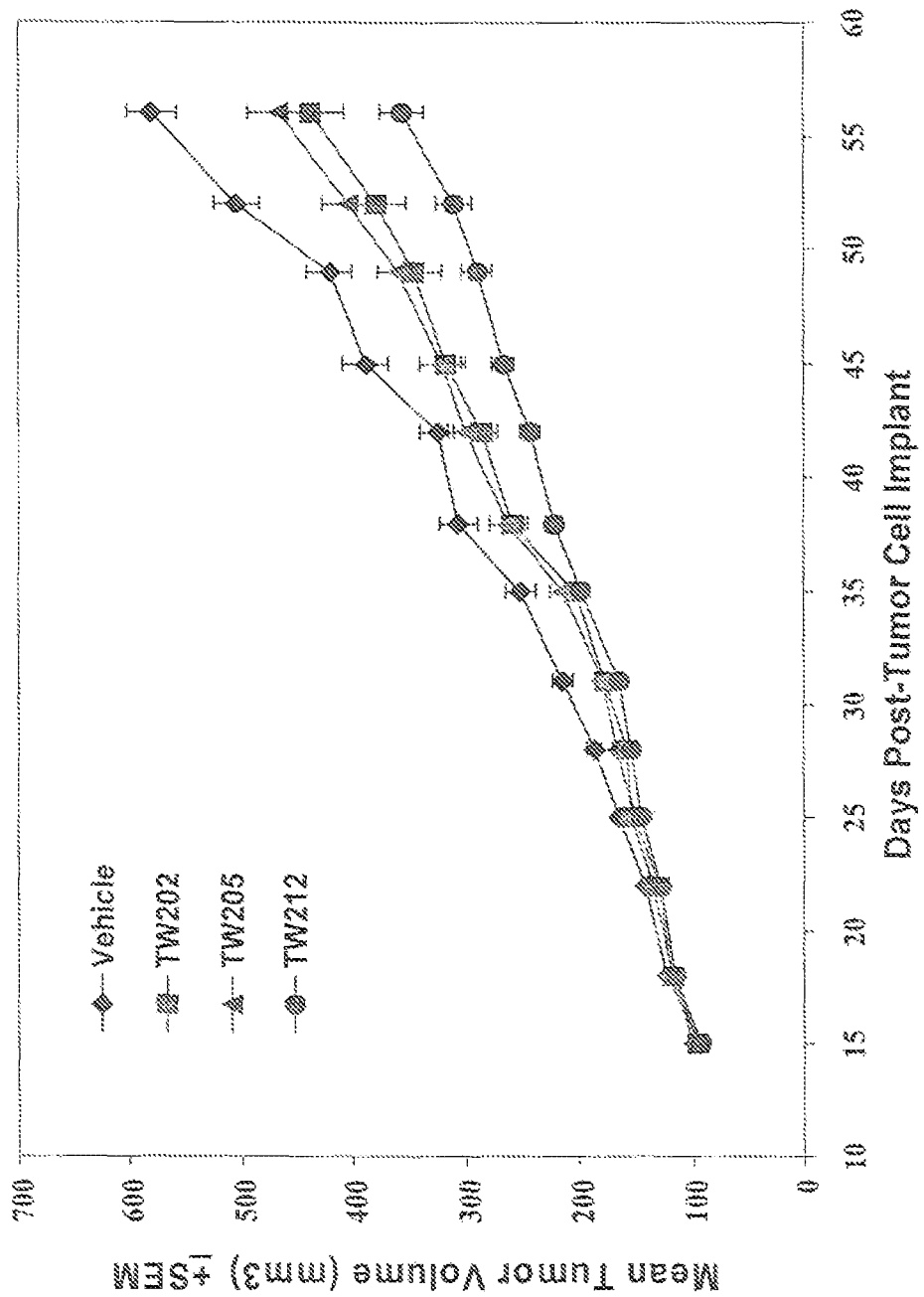
FIG. 1 Effect of anti-TWEAK antibodies on Panel human pancreatic carcinoma xenograft growth (Example 7)

The term "antibody" encompasses the various forms of antibody structures including, but not being limited to, whole antibodies, bispecific antibodies and antibody fragments. The antibody according to the invention is preferably a humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to TWEAK, namely being able to assemble together with a $V_H$ domain to a functional antigen binding site.

The terms "monoclonal antibody" or "monoclonal antibody composition" as used herein refer to a preparation of antibody molecules of a single amino acid composition.

The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a hamster CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising for example a mouse variable region and a human constant region. Such mouse/human chimeric antibodies are the product of expressed immunoglobulin genes comprising DNA segments encoding rat immunoglobulin variable regions and DNA segments encoding human immunoglobulin constant regions. Other forms of 20 "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., 25 Morrison, S.1., et al., Proc. Natl. Acad. Sci. USA 81 (1984) 6851-6855; U.S. Pat. Nos. 5,202,238 and 5,204,244.

The term "T cell epitope depleted antibody" refers to antibodies that were modified to remove or reduce immunogenicity by removing human T cell epitopes (peptide sequences within proteins with the capacity to bind to MHC Class II molecules). By this method, interactions between amino acid side chains of the peptide and specific binding pockets with the MHC class II binding groove are identified. The identified immunogenic regions are mutated to eliminate immunogenicity. Such methods are described in general in, e.g., WO 98/52976.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "CDR1H" denotes the CDR1 region of the heavy chain variable region calculated according to Kabat. CDR2L, CDR3H, etc. mean the respective regions from the heavy(H) or light(L) chain. For example, an antibody characterized by comprising CDR1H of SEQ ID NO:6 means that the antibody comprises this amino acid sequence as a heavy chain variable chain CDR1 region in its variable heavy chain. For example, an antibody characterized by comprising CDR1H of SEQ ID NO:6, CDR2H of SEQ ID NO:7, CDR3H of SEQ ID NO:8 means that the antibody comprises in its heavy chain as sequence of CDR1 SEQ ID NO:6, as sequence of CDR2 SEQ ID NO:7, and as sequence of CDR3 SEQ ID NO:8.

The terms "nucleic acid" or "nucleic acid molecule" as used herein are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided into the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described, e.g., by Boakle, R. J. et al., Nature 282 (1979) 742-743; Lukas, T. J. et al., J. Immunol. 127 (1981) 2555-2560; Brunhouse, R. and Cebra, J. J., Mol. Immunol. 16 (1979) 907-917; Burton, D. R. et al., Nature 288 (1980) 338-344; Thommesen, J. E. et al., Mol. Immunol. 37 (2000) 995-1004; Idusogie, E. E. et al., J. Immunol. 164 (2000) 4178-4184; Hezareh, M. et al., J. Virology 75 (2001) 12161-12168; Morgan, A. et al., Immunology 86 (1995) 319-324; EP 0 307 434. Such binding sites are, e.g., L234, L235, D270, N297, E318, K320, K322, P331, and P329 (numbering according to EU index of Kabat, see below). Antibodies of subclass IgG1, IgG2 and IgG3 usually show complement activation and C1q and C3 binding, whereas IgG4 does not activate the complement system and does not bind C1q and C3.

The antibody according to the invention preferably comprises an Fc part of human origin which is Fc part of a human antibody of the subclass IgG1.

The antibody according to the invention is characterized in that the constant chains are of human origin. Such constant chains are well known in the state of the art and e.g. described by Kabat (see e.g. Johnson, G. and Wu, T. T., Nucleic Acids Res. 28 (2000) 214-218). For example, a useful human heavy chain constant region comprises an amino acid sequence of SEQ ID NO:27 or 28. For example, a useful human light chain constant region comprises an amino acid sequence of a kappa-light chain constant region of SEQ ID NO:25. It is further preferred that the antibody is of hamster origin and comprises the antibody variable sequence frame of a hamster antibody according to Kabat (see e.g. Sequences of Proteins of Immunological Interest, Kabat, E. A. et al., 5$^{th}$ edition, DIANE Publishing (1992)).

The invention also includes a method for the treatment of a patient in need of therapy, characterized by administering to the patient a therapeutically effective amount of an antibody according to the invention.

The invention also includes the use of an antibody according to the invention for the preparation of a medicament for the treatment of cancer.

The invention also includes the use of an antibody according to the invention for the treatment of inflammatory diseases and of cancer, especially colon, lung, or pancreatic cancer.

A further embodiment of the invention is a method for the production of an antibody against TWEAK, characterized in that the sequence of a nucleic acid encoding the heavy chain of an antibody according to the invention and the nucleic acid encoding the light chain of said antibody are inserted into one or two expression vector(s), said vector(s) is/are inserted in a eukaryotic host cell, the encoded antibody is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif 17 (1999) 183-202; Geisse, S. et al., Protein Expr. Purif 8 (1996) 271-282; Kaufman, R. J., Mol. Biotechnol. 16 (2000) 151-160; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including alkaline/SDS treatment, CsCl banding, column chromatography, agarose gel electrophoresis, and others well known in the art. See Ausubel, F. et al. (eds.), Current Protocols in Molecular Biology, Greene Publishing and Wiley Interscience, New York (1987).

Expression in NS0 cells is described by, e.g., Barnes, L. M. et al., Cytotechnology 32 (2000) 109-123; Barnes, L. M. et al., Biotech. Bioeng. 73 (2001) 261-270. Transient expression is described by, e.g., Durocher, Y. et al., Nucl. Acids. Res. 30 (2002) E9. Cloning of variable domains is described by Orlandi, R. et al., Proc. Natl. Acad. Sci. USA 86 (1989) 3833-3837; Carter, P. et al., Proc. Natl. Acad. Sci. USA 89 (1992) 4285-4289; Norderhaug, L. et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Monoclonal antibodies are suitably separated from the culture medium by conventional immunoglobulin purification procedures such as, for example, protein A-Sepharose, hydroxylapatite chromatography, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Nucleic acid molecules encoding amino acid sequence variants of anti-TWEAK antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-TWEAK antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from cancer, especially from colon, lung, or pancreatic cancer.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer, especially from colon, lung, or pancreatic cancer.

The invention also provides the use of an antibody according to the invention in an effective amount for the manufacture of a pharmaceutical agent, preferably together with a pharmaceutically acceptable carrier, for the treatment of a patient suffering from cancer, especially from colon, lung or pancreatics cancer.

Description of the Sequences

TABLE 1

Antibody 202

| | |
|---|---|
| Hamster light chain | SEQ ID NO: 1 |
| CDR1L | SEQ ID NO: 2 |
| CDR2L | SEQ ID NO: 3 |
| CDR3L | SEQ ID NO: 4 |
| Hamster heavy chain | SEQ ID NO: 5 |
| CDR1H | SEQ ID NO: 6 |
| CDR2H | SEQ ID NO: 7 |
| CDR3H | SEQ ID NO: 8 |
| Humanized variant of light chain 202-LC1 | SEQ ID NO: 32 |
| Humanized variant of light chain 202-LC2 | SEQ ID NO: 33 |
| Humanized variant of light chain 202-LC3 | SEQ ID NO: 34 |
| Humanized variant of light chain 202-LC4 | SEQ ID NO: 35 |
| Humanized variant of heavy chain 202-HC1 | SEQ ID NO: 36 |
| Humanized variant of heavy chain 202-HC2 | SEQ ID NO: 37 |
| Humanized variant of heavy chain 202-HC3 | SEQ ID NO: 38 |
| Humanized variant of heavy chain 202-HC4 | SEQ ID NO: 39 |
| Humanized variant of heavy chain 202-HC5 | SEQ ID NO: 40 |
| Humanized variant of heavy chain 202-HC6 | SEQ ID NO: 41 |
| Humanized variant of heavy chain 202-HC7 | SEQ ID NO: 42 |
| Humanized variant of heavy chain 202-HC8 | SEQ ID NO: 43 |

TABLE 2

Antibody 205

| | |
|---|---|
| Hamster light chain | SEQ ID NO: 9 |
| CDR1L | SEQ ID NO: 10 |
| CDR2L | SEQ ID NO: 11 |
| CDR3L | SEQ ID NO: 12 |
| Hamster heavy chain | SEQ ID NO: 13 |
| CDR1H | SEQ ID NO: 14 |
| CDR2H | SEQ ID NO: 15 |
| CDR3H | SEQ ID NO: 16 |
| Humanized variant of light chain 205-LC1 | SEQ ID NO: 44 |
| Humanized variant of light chain 205-LC2 | SEQ ID NO: 45 |
| Humanized variant of light chain 205-LC3 | SEQ ID NO: 46 |
| Humanized variant of light chain 205-LC4 | SEQ ID NO: 47 |
| Humanized variant of heavy chain 205-HC1 | SEQ ID NO: 48 |
| Humanized variant of heavy chain 205-HC2 | SEQ ID NO: 49 |
| Humanized variant of heavy chain 205-HC3 | SEQ ID NO: 50 |
| Humanized variant of heavy chain 205-HC4 | SEQ ID NO: 51 |
| Humanized variant of heavy chain 205-HC5 | SEQ ID NO: 52 |
| Humanized variant of heavy chain 205-HC6 | SEQ ID NO: 53 |
| Humanized variant of heavy chain 205-HC7 | SEQ ID NO: 54 |

TABLE 3

Antibody 212

| | |
|---|---|
| Hamster light chain | SEQ ID NO: 17 |
| CDR1L | SEQ ID NO: 18 |
| CDR2L | SEQ ID NO: 19 |
| CDR3L | SEQ ID NO: 20 |
| Hamster heavy chain | SEQ ID NO: 21 |
| CDR1H | SEQ ID NO: 22 |
| CDR2H_NPS | SEQ ID NO: 23 |
| CDR2H_NPA | SEQ ID NO: 74 |
| CDR2H_SPS | SEQ ID NO: 75 |
| CDR3H | SEQ ID NO: 24 |
| Humanized variant of light chain 212-LC1 | SEQ ID NO: 55 |
| Humanized variant of light chain 212-LC2 | SEQ ID NO: 56 |
| Humanized variant of light chain 212-LC3 | SEQ ID NO: 57 |
| Humanized variant of light chain 212-LC4 | SEQ ID NO: 58 |
| Humanized variant of light chain 212-LC5 | SEQ ID NO: 59 |
| Humanized variant of light chain 212-LC6 | SEQ ID NO: 60 |
| Humanized variant of heavy chain 212-HC5 | SEQ ID NO: 61 |
| Humanized variant of heavy chain 212-HC6 | SEQ ID NO: 62 |
| Humanized variant of heavy chain 212-HC7 | SEQ ID NO: 63 |
| Humanized variant of heavy chain 212-HC8 | SEQ ID NO: 64 |
| Humanized variant of heavy chain 212-HC9 | SEQ ID NO: 65 |

TABLE 3-continued

Antibody 212

| | |
|---|---|
| Humanized variant of heavy chain 212-HC10 | SEQ ID NO: 66 |
| Humanized variant of heavy chain 212-HC11 | SEQ ID NO: 67 |
| Humanized variant of heavy chain 212-HC6NPA | SEQ ID NO: 68 |
| Humanized variant of heavy chain 212-HC6SPS | SEQ ID NO: 69 |
| Humanized variant of heavy chain 212-HC7NPA | SEQ ID NO: 70 |
| Humanized variant of heavy chain 212-HC7SPS | SEQ ID NO: 71 |
| Humanized variant of heavy chain 212-HC9NPA | SEQ ID NO: 72 |
| Humanized variant of heavy chain 212-HC9SPS | SEQ ID NO: 73 |

TABLE 4

Human constant regions

| | |
|---|---|
| Human kappa light chain | SEQ ID NO: 25 |
| Human lambda light chain | SEQ ID NO: 26 |
| Human IgG1 (Caucasian Allotype) | SEQ ID NO: 27 |
| Human IgG1 (Afroamerican Allotype) | SEQ ID NO: 28 |
| Human IgG1 LALA-Mutant (Caucasian Allotype) | SEQ ID NO: 29 |
| Human IgG4 | SEQ ID NO: 30 |
| Human IgG4 SPLE-Mutant | SEQ ID NO: 31 |

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Description of Immunization

Immunization of Armenian Hamsters with Human/Murine Tweak

Armenian hamsters were immunized with 50 µg recombinant human soluble TWEAK (amino acids 99-249) at day 0 with complete Freund's adjuvant, day 28 and day 56 (both with incomplete Freund's adjuvant) and with 50 µg recombinant mouse soluble TWEAK (amino acids 81-225) at day 84 with incomplete Freund's adjuvant by intraperitoneal injection. Blood was taken at days 108 and 91 and serum prepared, which was used for titer determination by ELISA (see below). Animals with highest titers were selected for boosting at day 112 by intravenous injection of 50 µg of recombinant mouse soluble TWEAK and antibodies were selected based on their ability to bind human and mouse TWEAK (Example 2), neutralize human and mouse TWEAK-Fn14 interaction (Examples 4 and 5), and inhibit IL8 secretion (Example 6). In addition, the half-life of the antibody-TWEAK complex was investigated (Example 3). Antitumor efficacy of the antibodies was tested in Panel human pancreatic carcinoma xenografts and ACHN renal carcinoma xenografts.

EXAMPLE 2

Binding to Human and Mouse TWEAK (ELISA)

Binding of anti-TWEAK antibodies to human and mouse TWEAK was determined by ELISA. Human or mouse recombinant TWEAK were immobilized on a 384-well Nunc Maxisorp plate at 1 µg/ml, 25 µl/well, in 0.5 M carbonate coating buffer, pH 9.5, by incubation overnight at 2-8° C. Blocking of the plate with PBS/1% BSA for 1 h at room temperature was followed by two wash steps (0.1% Tween® 20 in PBS) and incubation with anti-TWEAK antibodies at different concentrations in blocking buffer or hybridoma supernatants of said antibodies for 1 h at room temperature. After further four washes, antibodies were detected with anti-hamster-HRP antibody diluted 1:5000 in blocking buffer, for 1 h at room temperature. Signal was developed by addition of ABTS® (Roche Diagnostics GmbH) for 10-30 minutes after another four wash steps. Absorbance was read out at 405 nm.

EXAMPLE 3

Half-Life Determination of the Antibody-TWEAK Complexes Using Biacore

A Biacore 2000 instrument was used with a Biacore streptavidin coated sensor mounted into the system. The system buffer HBS-ET (10 mM HEPES pH 7.4, 150 mM NaCl, 1 mM EDTA, 0.05% Tween® 20) was used at a flow rate of 100 µl/min. The sample buffer was the system buffer. Biotinylated human soluble TWEAK and biotinylated murine soluble TWEAK was immobilized on different flow cells on the SA sensor at 150 RU each. The flow cell FC1 was used as a blank reference cell. Each antibody was injected into the system as an analyte at 100 nM at 100 µl/min for 2 min association time. The dissociation of the immunecomplexes were monitored for 5 min. The sensor surface was washed with HBS-ET for 10 seconds and regenerated using 2×2 minutes injections with 10 mM glycine pH 2.25. This procedure was done at 25° C. The kinetically rate limiting step of the complex dissociation phase in the interval [240s-300s] was taken to calculate the dissociation rate kd [1/s] (Biacore Evaluation Software 4.0). According to the equation $t1/2 \text{ diss} = \ln(2)/(60 \times kd)$, the half-life of each immunocomplexe in minutes was calculated. Results are shown in tables 5 and 6b.

TABLE 5

| Antibody | | Human TWEAK t/2 diss [min] 25° C. |
|---|---|---|
| TW202 | Hamster | 53 |
| TW202chi | Chimer[1] | n.d. |
| TW205 | Hamster | 30 |
| TW205chi | Chimer[1] | n.d. |
| TW212 | Hamster | 20 |
| TW212chi | Chimer[1] | 13 |

[1]human kappa light chain SEQ ID NO: 25 and human IgG1 SEQ ID NO: 27

EXAMPLE 4

Neutralization of TWEAK-Fn14 Interaction (Human)

Blocking of human TWEAK/human Fn14 interaction was shown by receptor interaction ELISA. 96-well Maxisorp® plates (Nunc) were coated with 100 µl 1 µg/ml human Fn14: Fc (extracellular domain of human Fn14 (amino acids 1-75) fused to Fc portion of human IgG1) in PBS per well for 1.5 h at room temperature and blocked with a solution of 5% FBS in PBS for 30 minutes at room temperature under shaking. In the meantime, human Flag-tagged soluble TWEAK (amino acids 106-249) at 2.5 ng/ml in blocking solution was incubated with different concentrations of anti-TWEAK antibodies or hybridoma supernatant for 2 h at room temperature under shaking. After washing the Fn14-coated plate once with wash buffer (0.1% Tween® 20 in PBS), 100 µl of the TWEAK-antibody solution were transferred to each well and the plate was incubated for 1 h at room temperature, followed by four washes with wash buffer. Wells were filled with 100 µl of anti-FLAG-HRP detection antibody, diluted 1:5000 in blocking buffer, and incubated for 1 h at room temperature. After four more wash steps, the signal was developed by addition of 100 µl 3,3,5,5-Tetramethylbenzidine (TMB) solution for approximately ten minutes. The reaction was stopped by adding 100 µl of 1 N HCl, and absorbance measured at 450 nm (reference wavelength 620 nm). Results are shown in table 6.

EXAMPLE 5

Neutralization of TWEAK-Fn14 Interaction (Mouse)

The mouse TWEAK/mouse Fn14 interaction ELISA followed a similar principle as described for the human proteins but used a different detection system, as mouse soluble TWEAK was not tagged. Briefly, Maxisorp plates were coated with mouse Fn14:Fc (extracellular domain of mouse Fn14 (amino acids 1-75) fused to Fc portion of human IgG1) as described above for human Fn14:Fc, followed by blocking and washing. Mouse soluble TWEAK at 4 ng/ml was pre-incubated with anti-TWEAK-antibodies or hybridoma supernatant in blocking buffer and 100 µl of the mixture were added per well of the Fn14-coated plate. After 1 h of incubation at room temperature and four washes, biotinylated anti-mouse TWEAK antibody at 125 ng/ml in blocking buffer was added for 1 h at room temperature, followed by another four wash steps. The TWEAK antibody was detected by incubation with streptavidin-HRP, diluted 1:5000 in blocking buffer, for 30 minutes at room temperature. Signal was developed and absorbance measured as described above. Results are shown in table 6.

EXAMPLE 6

IL-8 Secretion ELISA

Blocking of TWEAK activity by anti-TWEAK antibodies in a cellular system was shown in an IL-8 secretion assay using A375 melanoma cells. 10,000 A375 cells (ATCC #CRL1619) were seeded per well of 96-well cell culture plate in 100 µl of growth medium (DMEM with 4.5 g/L glucose, with pyruvate and GlutaMAX™/10% FBS) and incubated at 37° C./5% $CO_2$ for 48 h. Human recombinant soluble TWEAK was pre-incubated at 300 ng/ml with different concentrations of anti-TWEAK antibodies in growth medium for 30 minutes at room temperature. Then, 50 µl of the mixture were added to each well of the cell plate, followed by another 48 h-incubation to allow for IL-8 secretion. 20 µl of the cell supernatant were removed after centrifuging the plate for five minutes at 200×g and mixed with 980 µl of RD5P Calibrator Diluent from the "CXCL8 Quantikine ELISA" kit (R&D Systems). IL-8 was detected by the ELISA according to the manufacturer's instructions. Results are shown in table 6.

TABLE 6a

| Antibody | | Interaction Inhibition | | IL-8 Secretion |
|---|---|---|---|---|
| | | Human TWEAK $IC_{50}$ [ng/ml] | Murine TWEAK $IC_{50}$ [ng/ml] | $IC_{50}$ [ng/ml] |
| TW-202 | Hamster | 9.2 | 9.0 | 146 |
| TW-202chi | Chimer | 11.8 | 11.8 | 269 |
| TW-205 | Hamster | 8.8 | 5.1 | 151 |
| TW-205chi | Chimer | 11.8 | 5.9 | 195 |

TABLE 6a-continued

| Antibody | | Interaction Inhibition | | IL-8 Secretion IC$_{50}$ [ng/ml] |
|---|---|---|---|---|
| | | Human TWEAK IC$_{50}$ [ng/ml] | Murine TWEAK IC$_{50}$ [ng/ml] | |
| TW-212 | Hamster | 15.1 | 4.6 | 112 |
| TW-212chi | Chimer | 13.4 | 5.7 | 111 |

TABLE 6b

| Antibody | Interaction Inhibition | | | Biacore |
|---|---|---|---|---|
| | Human TWEAK IC$_{50}$ [ng/ml] | Murine TWEAK IC$_{50}$ [ng/ml] | IL-8 Secretion IC$_{50}$ [ng/ml] | Human TWEAK t/2 diss. [min] 25° C. |
| 15 | 14 | 5 | 141 | 18 |
| 16 | 22 | 7 | 163 | 15 |
| 17 | 14 | 6 | 146 | 18 |
| 18 | 16 | 6 | 189 | 16 |
| 19 | 15 | 7 | 253 | 17 |
| 20 | 35 | 14 | 401 | 15 |
| 21 | 12 | 5 | 224 | 17 |
| 22 | 17 | 5 | 249 | 14 |
| 23 | 13 | 6 | 242 | 17 |
| 24 | 20 | 8 | 165 | 15 |
| 25 | 42 | 18 | 475 | 17 |
| 26 | 94 | 36 | 222 | 16 |

TABLE 6c

| Antibody | Variable light chain sequence | Variable heavy chain sequence |
|---|---|---|
| 15 | SEQ ID NO: 57 | SEQ ID NO: 68 |
| 16 | SEQ ID NO: 57 | SEQ ID NO: 69 |
| 17 | SEQ ID NO: 57 | SEQ ID NO: 70 |
| 18 | SEQ ID NO: 57 | SEQ ID NO: 71 |
| 19 | SEQ ID NO: 57 | SEQ ID NO: 72 |
| 20 | SEQ ID NO: 57 | SEQ ID NO: 73 |
| 21 | SEQ ID NO: 58 | SEQ ID NO: 68 |
| 22 | SEQ ID NO: 58 | SEQ ID NO: 69 |
| 23 | SEQ ID NO: 58 | SEQ ID NO: 70 |
| 24 | SEQ ID NO: 58 | SEQ ID NO: 71 |
| 25 | SEQ ID NO: 58 | SEQ ID NO: 72 |
| 26 | SEQ ID NO: 58 | SEQ ID NO: 73 |

EXAMPLE 7

Antitumor Efficacy Anti-Tweak Antibodies Against Panc1 Human Pancreatic Carcinoma Xenograft Growth Study design: Panc1 cells ($1 \times 10^7$ cells/mouse) were implanted into SCID-beige mice sc on study day 0 with matrigel (1:1). Treatments started on day 15 post implant. Study ended on day 56.

Groups

Vehicle ip, 2×/wk, n=10

20 mg/kg TW202, ip, 2×/wk, n=10

20 mg/kg TW205, ip, 2×/wk, n=10

20 mg/kg TW212, ip, 2×/wk, n=10

Individual tumors are weighed at the end of study. Results are shown in table 7.

TABLE 7

| Panc1 | Mean tumor volume [mm3] | SD | SEM |
|---|---|---|---|
| Vehicle | 580.51 | ±69.74 | ±22.05 |
| TW202 | 437.20 | ±95.83 | ±30.30 |
| TW205 | 456.40 | ±90.84 | ±28.72 |
| TW212 | 356.60 | ±62.50 | ±19.76 |

Tumor volumes vs. days post-tumor cell implant are shown in FIG. 1.

EXAMPLE 8

Effect of Anti-TWEAK Antibodies on ACHN Renal Carcinoma Xenograft Growth

Study design: ACHN cells ($1 \times 10^7$ cells/mouse) implanted with matrigel (1:1) into athymic nude mice sc on study day 0. Treatments started on day 10 post implant. Study ended on day 40.

Groups:

Vehicle ip, 2×/wk, n=10

TW202 (20 mg/kg) ip, 2×/wk, n=10

TW205 (20 mg/kg), ip, 2×/wk, n=10

TW212 (20 mg/kg) ip, 2×/wk, n=10

The average volume of the tumors are weighed at the end of study. Results are shown in table 8.

TABLE 8

| ACHN | Mean tumor volume [mm3] | SD | SEM |
|---|---|---|---|
| Vehicle | 596.04 | ±241.68 | ±76.43 |
| TW202 | 161.28 | ±89.44 | ±28.28 |
| TW205 | 151.64 | ±82.46 | ±26.08 |
| TW212 | 217.12 | ±189.73 | ±60.00 |

Figure 2:
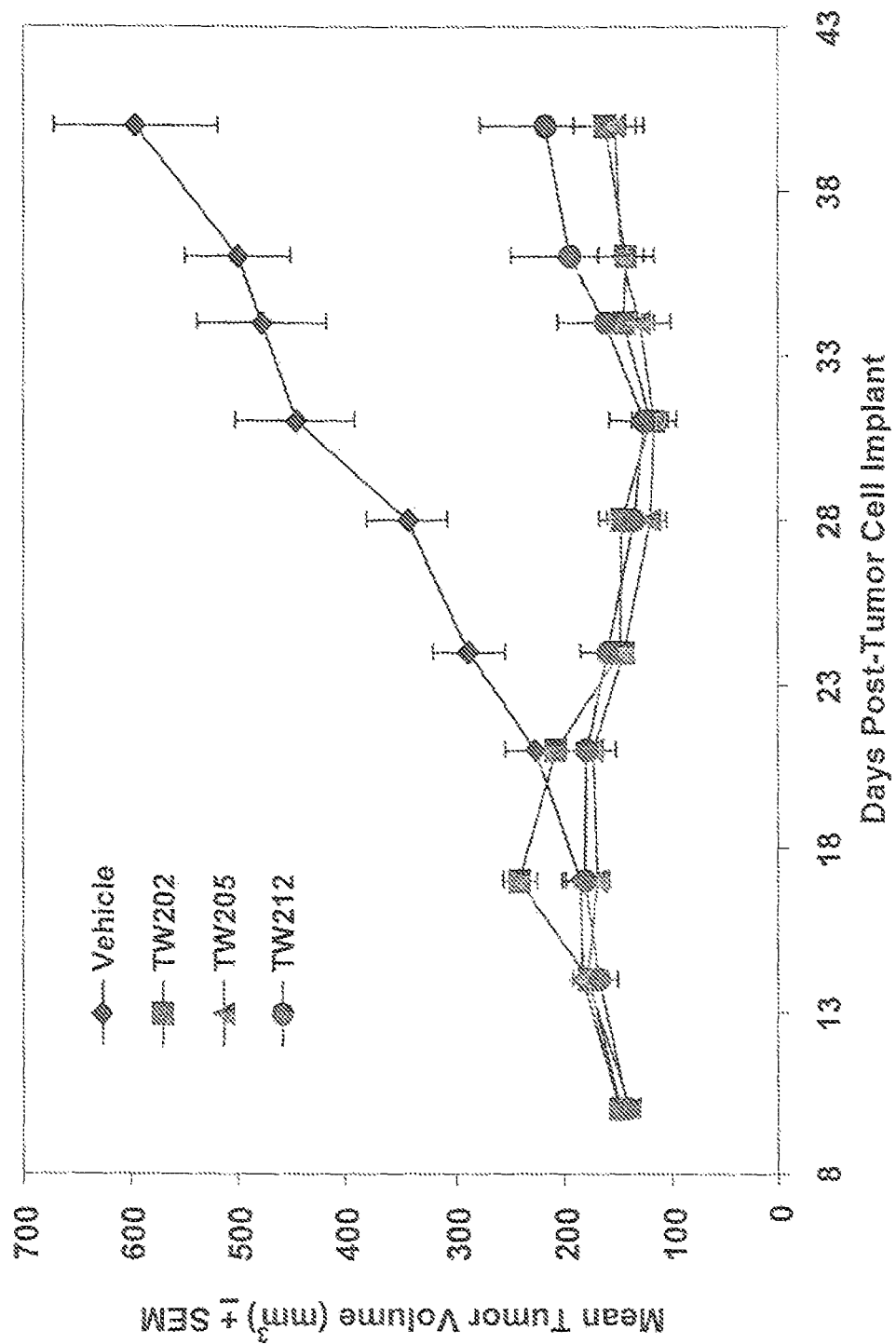
FIG. 2 Effect of anti-TWEAK antibodies on ACHN human renal carcinoma xenograft growth (Example 8).

Tumor volumes vs. days post-tumor cell implant are shown in FIG. 2.

The invention claimed is:

1. An isolated, humanized antibody that binds to human TWEAK, comprising the variable heavy chain amino acid sequence of SEQ ID NO: 68.

2. An isolated, humanized antibody that binds to human TWEAK, comprising the combination of variable light chain amino acid sequence/variable heavy chain amino acid sequence of SEQ ID NO: 58/SEQ ID NO: 68.

3. An isolated, humanized antibody that binds to human TWEAK, comprising a variable heavy chain comprising CDR1H with the amino acid sequence of SEQ ID NO:22, CDR2H with the amino acid sequence of SEQ ID NO:74, CDR3H with the amino acid sequence of SEQ ID NO:24, and a variable light chain comprising CDR1L with the amino acid sequence of SEQ ID NO:18, CDR2L with the amino acid sequence of SEQ ID NO:19, and CDR3L with the amino acid sequence of SEQ ID NO:20.

4. A composition comprising an antibody of claim 3 and a pharmaceutically acceptable carrier.

* * * * *

SEQUENCE LISTING

<160> NUMBER OF SEQ ID NOS: 75

<210> SEQ ID NO 1
<211> LENGTH: 217
<212> TYPE: PRT
<213> ORGANISM: Unknown

```
<220> FEATURE:
<223> OTHER INFORMATION: Description of Unknown: Hamster
      polypeptide

<400> SEQUENCE: 1

Gln Pro Val Leu Thr Gln Ser Pro Ser Ala Ser Ala Ser Leu Arg Ala
1               5                   10                  15

Ser Val Lys Leu Thr Cys Thr Leu Ser Ser Gln His Ser Thr Tyr Tyr
            20                  25                  30

Ile Glu Trp Tyr Gln Gln Arg Pro Asp Lys Ala Pro Lys Tyr Val Met
        35                  40                  45

Tyr Leu Asp Ser Asp Gly Ser His Ile Lys Gly Asp Gly Ile Pro Asp
    50                  55                  60

Arg Phe Ser Gly Ser Ser Ser Gly Ala His Arg Tyr Leu Ser Ile Ser
65                  70                  75                  80

Asn Leu Gln Pro Glu Asp Glu Ala Ile Tyr His Cys Gly Val Tyr Asp
                85                  90                  95

Ser Thr Ala Gly Ala Val Phe Gly Ser Gly Thr Gln Leu Thr Val Leu
            100                 105                 110

Gly Gly Pro Lys Ser Ser Pro Lys Val Thr Val Phe Pro Pro Ser Pro
        115                 120                 125

Glu Glu Leu Arg Thr Asn Lys Ala Thr Leu Val Cys Leu Val Asn Asp
    130                 135                 140

Phe Tyr Pro Gly Ser Ala Thr Val Thr Trp Lys Ala Asn Gly Ala Thr
145                 150                 155                 160

Ile Asn Asp Gly Val Lys Thr Thr Lys Pro Ser Lys Gln Gly Gln Asn
                165                 170                 175

Tyr Met Thr Ser Ser Tyr Leu Ser Leu Thr Ala Asp Gln Trp Lys Ser
            180                 185                 190

His Asn Arg Val Ser Cys Gln Val Thr His Glu Gly Glu Thr Val Glu
        195                 200                 205

Lys Ser Leu Ser Pro Ala Glu Cys Leu
    210                 215

<210> SEQ ID NO 2
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 2

Thr Leu Ser Ser Gln His Ser Thr Tyr Tyr Ile Glu
1               5                   10

<210> SEQ ID NO 3
<211> LENGTH: 11
<212> TYPE: PRT
<213> ORGANISM: Unknown
<220> FEATURE:
<223> OTHER INFORMATION: Description of Unknown: Hamster
      peptide

<400> SEQUENCE: 3

Leu Asp Ser Asp Gly Ser His Ile Lys Gly Asp
1               5                   10
```

```
<210> SEQ ID NO 4
<211> LENGTH: 10
<212> TYPE: PRT
<213> ORGANISM: Unknown
<220> FEATURE:
<223> OTHER INFORMATION: Description of Unknown: Hamster
      peptide

<400> SEQUENCE: 4

Gly Val Tyr Asp Ser Thr Ala Gly Ala Val
1               5                   10

<210> SEQ ID NO 5
<211> LENGTH: 460
<212> TYPE: PRT
<213> ORGANISM: Unknown
<220> FEATURE:
<223> OTHER INFORMATION: Description of Unknown: Hamster
      polypeptide

<400> SEQUENCE: 5

Gln Leu Gln Leu Gln Glu Ser Gly Leu Gly Leu Val Lys Pro Ser Gln
1               5                   10                  15

Ser Leu Thr Leu Thr Cys Ser Val Thr Gly Phe Ser Ile Thr Thr Pro
            20                  25                  30

Asp Tyr Ser Trp His Trp Ile Arg Gln Leu Pro Gly Gln Thr Leu Glu
        35                  40                  45

Trp Met Gly Phe Leu Tyr Tyr Glu Gly Asp Thr Tyr Tyr Asn Pro Ser
    50                  55                  60

Leu Lys Ser Arg Ile Ser Ile Ala Arg Asp Ala Ser Lys Asn Gln Phe
65                  70                  75                  80

Phe Leu Gln Leu Lys Ala Val Thr Thr Glu Asp Thr Ala Thr Tyr Phe
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Leu Ala Thr Thr Thr Ala Pro
        115                 120                 125

Ser Val Tyr Pro Leu Ala Pro Ala Cys Asp Ser Thr Thr Ser Thr Thr
    130                 135                 140

Asp Thr Val Thr Leu Gly Cys Leu Val Lys Gly Tyr Phe Pro Glu Pro
145                 150                 155                 160

Val Thr Val Ser Trp Asn Ser Gly Ala Leu Thr Ser Gly Val His Thr
                165                 170                 175

Phe Pro Ser Val Leu His Ser Gly Leu Tyr Ser Leu Ser Ser Ser Val
            180                 185                 190

Thr Val Pro Ser Ser Thr Trp Pro Lys Gln Pro Ile Thr Cys Asn Val
        195                 200                 205

Ala His Pro Ala Ser Ser Thr Lys Val Asp Lys Ile Glu Pro Arg
    210                 215                 220

Thr Asp Thr Asp Thr Cys Pro Asn Pro Pro Asp Pro Cys Pro Thr Cys
225                 230                 235                 240

Pro Thr Pro Asp Leu Leu Gly Gly Pro Ser Val Phe Ile Phe Pro Pro
                245                 250                 255

Lys Pro Lys Asp Val Leu Met Ile Ser Leu Thr Pro Lys Ile Thr Cys
            260                 265                 270

Val Val Val Asp Val Ser Glu Glu Glu Pro Asp Val Gln Phe Asn Trp
        275                 280                 285
```

```
Tyr Val Asn Asn Val Glu Asp Lys Thr Ala Gln Thr Glu Thr Arg Gln
        290                 295                 300

Arg Gln Tyr Asn Ser Thr Tyr Arg Val Val Ser Val Leu Pro Ile Lys
305                 310                 315                 320

His Gln Asp Trp Met Ser Gly Lys Val Phe Lys Cys Lys Val Asn Asn
                325                 330                 335

Asn Ala Leu Pro Ser Pro Ile Glu Lys Thr Ile Ser Lys Pro Arg Gly
            340                 345                 350

Gln Val Arg Val Pro Gln Ile Tyr Thr Phe Pro Pro Ile Glu Gln
        355                 360                 365

Thr Val Lys Lys Asp Val Ser Val Thr Cys Leu Val Thr Gly Phe Leu
370                 375                 380

Pro Gln Asp Ile His Val Glu Trp Glu Ser Asn Gly Gln Pro Gln Pro
385                 390                 395                 400

Glu Gln Asn Tyr Lys Asn Thr Gln Pro Val Leu Asp Ser Asp Gly Ser
                405                 410                 415

Tyr Phe Leu Tyr Ser Lys Leu Asn Val Pro Lys Ser Arg Trp Asp Gln
            420                 425                 430

Gly Asp Ser Phe Thr Cys Ser Val Ile His Glu Ala Leu His Asn His
                435                 440                 445

His Met Thr Lys Thr Ile Ser Arg Ser Leu Gly Asn
    450                 455                 460

<210> SEQ ID NO 6
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 6

Gly Phe Ser Ile Thr Thr Pro Asp Tyr Ser Trp His
1               5                   10

<210> SEQ ID NO 7
<211> LENGTH: 16
<212> TYPE: PRT
<213> ORGANISM: Unknown
<220> FEATURE:
<223> OTHER INFORMATION: Description of Unknown: Hamster
      peptide

<400> SEQUENCE: 7

Phe Leu Tyr Tyr Glu Gly Asp Thr Tyr Tyr Asn Pro Ser Leu Lys Ser
1               5                   10                  15

<210> SEQ ID NO 8
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 8

Arg Lys Tyr Ser Gly Tyr Gly Asn Trp Phe Ala Tyr
1               5                   10

<210> SEQ ID NO 9
<211> LENGTH: 217
<212> TYPE: PRT
```

```
<213> ORGANISM: Unknown
<220> FEATURE:
<223> OTHER INFORMATION: Description of Unknown: Hamster
      polypeptide

<400> SEQUENCE: 9

Gln Pro Val Leu Thr Gln Ala Pro Ser Ala Ser Ala Ser Leu Arg Ala
1               5                   10                  15

Ser Val Lys Leu Thr Cys Thr Leu Ser Ser Gln His Ser Thr Tyr Tyr
            20                  25                  30

Ile Glu Trp Tyr Gln Gln His Pro Asp Lys Ala Pro Arg Tyr Val Met
        35                  40                  45

Tyr Val Asp Ser Asp Gly Ser His Ile Lys Gly Asp Gly Val Pro Asp
    50                  55                  60

Arg Phe Ser Gly Ser Ser Gly Ala Arg Arg Tyr Leu Ser Ile Ser
65                  70                  75                  80

Asn Leu Gln Pro Glu Asp Glu Ala Ile Tyr His Cys Gly Val Tyr Asp
                85                  90                  95

Ser Thr Ala Gly Ala Val Phe Gly Ser Gly Thr Gln Leu Thr Val Leu
            100                 105                 110

Gly Gly Pro Lys Ser Ser Pro Lys Val Thr Val Phe Pro Pro Ser Pro
        115                 120                 125

Glu Glu Leu Arg Thr Asn Lys Ala Thr Leu Val Cys Leu Val Asn Asp
130                 135                 140

Phe Tyr Pro Gly Ser Ala Thr Val Thr Trp Lys Ala Asn Gly Ala Thr
145                 150                 155                 160

Ile Asn Asp Gly Val Lys Thr Thr Lys Pro Ser Lys Gln Gly Gln Asn
                165                 170                 175

Tyr Met Thr Ser Ser Tyr Leu Ser Leu Thr Ala Asp Gln Trp Lys Ser
            180                 185                 190

His Asn Arg Val Ser Cys Gln Val Thr His Glu Gly Glu Thr Val Glu
        195                 200                 205

Lys Ser Leu Ser Pro Ala Glu Cys Leu
    210                 215

<210> SEQ ID NO 10
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 10

Thr Leu Ser Ser Gln His Ser Thr Tyr Tyr Ile Glu
1               5                   10

<210> SEQ ID NO 11
<211> LENGTH: 11
<212> TYPE: PRT
<213> ORGANISM: Unknown
<220> FEATURE:
<223> OTHER INFORMATION: Description of Unknown: Hamster
      peptide

<400> SEQUENCE: 11

Val Asp Ser Asp Gly Ser His Ile Lys Gly Asp
1               5                   10

<210> SEQ ID NO 12
```

```
<211> LENGTH: 10
<212> TYPE: PRT
<213> ORGANISM: Unknown
<220> FEATURE:
<223> OTHER INFORMATION: Description of Unknown: Hamster
      peptide

<400> SEQUENCE: 12

Gly Val Tyr Asp Ser Thr Ala Gly Ala Val
1               5                   10

<210> SEQ ID NO 13
<211> LENGTH: 460
<212> TYPE: PRT
<213> ORGANISM: Unknown
<220> FEATURE:
<223> OTHER INFORMATION: Description of Unknown: Hamster
      polypeptide

<400> SEQUENCE: 13

Gln Ile His Leu Gln Glu Ser Gly Leu Gly Leu Val Lys Pro Ser Gln
1               5                   10                  15

Ser Leu Thr Leu Thr Cys Ser Val Thr Gly Phe Ser Ile Thr Thr Pro
            20                  25                  30

Asp Tyr Ser Trp His Trp Ile Arg Gln Phe Pro Gly Gln Thr Leu Glu
        35                  40                  45

Trp Met Gly Phe Leu Tyr Tyr Glu Gly Asp Thr Tyr Tyr Asn Pro Ser
    50                  55                  60

Leu Lys Ser Arg Ile Ser Ile Ala Arg Asp Ala Ser Lys Asn Gln Phe
65                  70                  75                  80

Phe Leu Gln Leu Lys Ser Val Thr Thr Glu Asp Thr Ala Thr Tyr Phe
                85                  90                  95

Cys Val Arg Arg Lys Tyr Ser Gly Tyr Gly Asn Trp Phe Ala Tyr Trp
            100                 105                 110

Gly Gln Gly Thr Gln Val Thr Val Ser Ser Ala Thr Thr Thr Ala Pro
        115                 120                 125

Ser Val Tyr Pro Leu Ala Pro Ala Cys Asp Ser Thr Thr Ser Thr Thr
    130                 135                 140

Asp Thr Val Thr Leu Gly Cys Leu Val Lys Gly Tyr Phe Pro Glu Pro
145                 150                 155                 160

Val Thr Val Ser Trp Asn Ser Gly Ala Leu Thr Ser Gly Val His Thr
                165                 170                 175

Phe Pro Ser Val Leu His Ser Gly Leu Tyr Ser Leu Ser Ser Ser Val
            180                 185                 190

Thr Val Pro Ser Ser Thr Trp Pro Lys Gln Pro Ile Thr Cys Asn Val
        195                 200                 205

Ala His Pro Ala Ser Ser Thr Lys Val Asp Lys Lys Ile Glu Pro Arg
    210                 215                 220

Thr Asp Thr Asp Thr Cys Pro Asn Pro Pro Asp Pro Cys Pro Thr Cys
225                 230                 235                 240

Pro Thr Pro Asp Leu Leu Gly Gly Pro Ser Val Phe Ile Phe Pro Pro
                245                 250                 255

Lys Pro Lys Asp Val Leu Met Ile Ser Leu Thr Pro Lys Ile Thr Cys
            260                 265                 270

Val Val Val Asp Val Ser Glu Glu Pro Asp Val Gln Phe Asn Trp
        275                 280                 285

Tyr Val Asn Asn Val Glu Asp Lys Thr Ala Gln Thr Glu Thr Arg Gln
    290                 295                 300
```

```
Arg Gln Tyr Asn Ser Thr Tyr Arg Val Val Ser Val Leu Pro Ile Lys
305                 310                 315                 320

His Gln Asp Trp Met Ser Gly Lys Val Phe Lys Cys Lys Val Asn Asn
            325                 330                 335

Asn Ala Leu Pro Ser Pro Ile Glu Lys Thr Ile Ser Lys Pro Arg Gly
        340                 345                 350

Gln Val Arg Val Pro Gln Ile Tyr Thr Phe Pro Pro Pro Ile Glu Gln
    355                 360                 365

Thr Val Lys Lys Asp Val Ser Val Thr Cys Leu Val Thr Gly Phe Leu
370                 375                 380

Pro Gln Asp Ile His Val Glu Trp Glu Ser Asn Gly Gln Pro Gln Pro
385                 390                 395                 400

Glu Gln Asn Tyr Lys Asn Thr Gln Pro Val Leu Asp Ser Asp Gly Ser
            405                 410                 415

Tyr Phe Leu Tyr Ser Lys Leu Asn Val Pro Lys Ser Arg Trp Asp Gln
        420                 425                 430

Gly Asp Ser Phe Thr Cys Ser Val Ile His Glu Ala Leu His Asn His
    435                 440                 445

His Met Thr Lys Thr Ile Ser Arg Ser Leu Gly Asn
450                 455                 460

<210> SEQ ID NO 14
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 14

Gly Phe Ser Ile Thr Thr Pro Asp Tyr Ser Trp His
1               5                   10

<210> SEQ ID NO 15
<211> LENGTH: 16
<212> TYPE: PRT
<213> ORGANISM: Unknown
<220> FEATURE:
<223> OTHER INFORMATION: Description of Unknown: Hamster
      peptide

<400> SEQUENCE: 15

Phe Leu Tyr Tyr Glu Gly Asp Thr Tyr Tyr Asn Pro Ser Leu Lys Ser
1               5                   10                  15

<210> SEQ ID NO 16
<211> LENGTH: 12
<212> TYPE: PRT
<213> ORGANISM: Unknown
<220> FEATURE:
<223> OTHER INFORMATION: Description of Unknown: Hamster
      peptide

<400> SEQUENCE: 16

Arg Lys Tyr Ser Gly Tyr Gly Asn Trp Phe Ala Tyr
1               5                   10

<210> SEQ ID NO 17
<211> LENGTH: 218
<212> TYPE: PRT
<213> ORGANISM: Unknown
<220> FEATURE:
```

```
<223> OTHER INFORMATION: Description of Unknown: Hamster
      polypeptide

<400> SEQUENCE: 17

Asp Ile Val Leu Thr Gln Ser Pro Ala Tyr Leu Thr Met Ser Pro Gly
1               5                   10                  15

Gln Thr Thr Thr Ile Ser Cys Lys Ala Ser Gln Ser Val Ser Ile Gly
            20                  25                  30

Pro Ile His Leu Met His Trp Tyr Gln Gln Lys Pro Gly Gln Pro Pro
        35                  40                  45

Arg Leu Leu Ile Tyr Gly Ala Ser Asn Pro Glu Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ala Asp Ala Ala Thr Tyr Phe Cys Gln Gln Gly Lys
                85                  90                  95

Glu Ser Pro Arg Thr Phe Gly Pro Gly Thr Lys Leu Glu Ile Thr Arg
            100                 105                 110

Ala Asp Ala Lys Pro Thr Val Ser Ile Phe Pro Pro Ser Ser Glu Gln
            115                 120                 125

Leu Gly Thr Gly Ser Ala Thr Leu Val Cys Phe Val Asn Asn Phe Tyr
    130                 135                 140

Pro Lys Asp Ile Asn Val Lys Trp Lys Val Asp Gly Ser Glu Lys Arg
145                 150                 155                 160

Asp Gly Val Leu Gln Ser Val Thr Asp Gln Asp Ser Lys Asp Ser Thr
                165                 170                 175

Tyr Ser Leu Ser Ser Thr Leu Ser Leu Thr Lys Ala Asp Tyr Glu Arg
            180                 185                 190

His Asn Leu Tyr Thr Cys Glu Val Thr His Lys Thr Ser Thr Ala Ala
        195                 200                 205

Ile Val Lys Thr Leu Asn Arg Asn Glu Cys
    210                 215

<210> SEQ ID NO 18
<211> LENGTH: 15
<212> TYPE: PRT
<213> ORGANISM: Unknown
<220> FEATURE:
<223> OTHER INFORMATION: Description of Unknown: Hamster
      peptide

<400> SEQUENCE: 18

Lys Ala Ser Gln Ser Val Ser Ile Gly Pro Ile His Leu Met His
1               5                   10                  15

<210> SEQ ID NO 19
<211> LENGTH: 7
<212> TYPE: PRT
<213> ORGANISM: Unknown
<220> FEATURE:
<223> OTHER INFORMATION: Description of Unknown: Hamster
      peptide

<400> SEQUENCE: 19

Gly Ala Ser Asn Pro Glu Ser
1               5

<210> SEQ ID NO 20
<211> LENGTH: 9
<212> TYPE: PRT
```

```
<213> ORGANISM: Unknown
<220> FEATURE:
<223> OTHER INFORMATION: Description of Unknown: Hamster
      peptide

<400> SEQUENCE: 20

Gln Gln Gly Lys Glu Ser Pro Arg Thr
1               5

<210> SEQ ID NO 21
<211> LENGTH: 446
<212> TYPE: PRT
<213> ORGANISM: Unknown
<220> FEATURE:
<223> OTHER INFORMATION: Description of Unknown: Hamster
      polypeptide

<400> SEQUENCE: 21

Gln Val Gln Leu Gln Glu Ser Gly Pro Gly Leu Leu Lys Pro Ala Gln
1               5                   10                  15

Ser Leu Ser Leu Thr Cys Thr Val Thr Gly Tyr Ser Ile Arg Ser Gly
                20                  25                  30

Tyr Trp Trp Ser Trp Ile Arg Gln Gln Pro Gly Lys Gly Leu Glu Trp
            35                  40                  45

Met Gly Gln Ile Tyr Asn Lys Gly Asn Thr Asp Asn Pro Ser Leu
    50                  55                  60

Lys Ser Gln Ile Thr Met Thr Val Asp Thr Ser Lys Asn Gln Phe Phe
65                  70                  75                  80

Leu Arg Leu Arg Ser Val Thr Thr Glu Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Ile Gln Val Thr Val Ser Ser Ala Thr Thr Ala Pro Ser Val Tyr
            115                 120                 125

Pro Leu Ala Pro Ala Cys Asp Ser Thr Thr Ser Thr Asn Thr Val
            130                 135                 140

Thr Leu Gly Cys Leu Val Lys Gly Tyr Phe Pro Glu Pro Val Thr Val
145                 150                 155                 160

Ser Trp Asn Ser Gly Ala Leu Thr Ser Gly Val His Thr Phe Pro Ser
                165                 170                 175

Val Leu His Ser Gly Leu Tyr Ser Leu Ser Ser Val Thr Val Pro
            180                 185                 190

Ser Ser Thr Trp Pro Ser Gln Thr Val Thr Cys Asn Val Ala His Pro
                195                 200                 205

Ala Ser Ser Thr Lys Val Asp Lys Lys Ile Val Pro Gly Asp Gly Ser
            210                 215                 220

Gly Cys Lys Pro Cys Thr Cys Pro Gly Pro Glu Val Ser Ser Val Phe
225                 230                 235                 240

Ile Phe Pro Pro Lys Pro Lys Asp Val Leu Thr Ile Ser Leu Ser Pro
                245                 250                 255

Lys Val Thr Cys Val Val Val Asp Ile Ser Gln Asp Asp Pro Glu Val
            260                 265                 270

Gln Phe Ser Trp Phe Ile Asp Gly Lys Glu Val His Thr Ala Val Thr
            275                 280                 285

Gln Pro Arg Glu Glu Gln Phe Asn Ser Thr Tyr Arg Met Val Ser Val
    290                 295                 300

Leu Pro Ile Leu His Gln Asp Trp Leu Asn Gly Lys Glu Phe Lys Cys
```

```
                305                 310                 315                 320
Lys Val Asn Ser Pro Ala Phe Pro Val Pro Ile Glu Lys Thr Ile Ser
                325                 330                 335

Lys Arg Arg Gly Gln Leu Gln Val Pro Gln Val Tyr Thr Met Pro Pro
                340                 345                 350

Pro Lys Glu Gln Leu Thr Gln Ser Gln Val Ser Leu Thr Cys Met Ile
                355                 360                 365

Lys Gly Phe Tyr Pro Glu Asp Ile Asp Val Ala Trp Gln Lys Asn Gly
            370                 375                 380

Gln Pro Glu Gln Ser Phe Lys Asn Thr Pro Pro Val Leu Asp Thr Asp
385                 390                 395                 400

Glu Thr Tyr Phe Leu Tyr Ser Lys Leu Asp Val Lys Lys Asp Asp Trp
                405                 410                 415

Glu Lys Gly Asp Thr Phe Thr Cys Ser Val Val His Glu Ala Leu His
            420                 425                 430

Asn His His Thr Glu Lys Thr Leu Ser Gln Arg Pro Gly Lys
            435                 440                 445

<210> SEQ ID NO 22
<211> LENGTH: 11
<212> TYPE: PRT
<213> ORGANISM: Unknown
<220> FEATURE:
<223> OTHER INFORMATION: Description of Unknown: Hamster
      peptide

<400> SEQUENCE: 22

Gly Tyr Ser Ile Arg Ser Gly Tyr Trp Trp Ser
1               5                   10

<210> SEQ ID NO 23
<211> LENGTH: 16
<212> TYPE: PRT
<213> ORGANISM: Unknown
<220> FEATURE:
<223> OTHER INFORMATION: Description of Unknown: Hamster
      peptide

<400> SEQUENCE: 23

Gln Ile Tyr Asn Lys Gly Asn Thr Asp Asn Pro Ser Leu Lys Ser
1               5                   10                  15

<210> SEQ ID NO 24
<211> LENGTH: 10
<212> TYPE: PRT
<213> ORGANISM: Unknown
<220> FEATURE:
<223> OTHER INFORMATION: Description of Unknown: Hamster
      peptide

<400> SEQUENCE: 24

Val Phe Trp Asp Asp Ala Tyr Phe Asp Val
1               5                   10

<210> SEQ ID NO 25
<211> LENGTH: 107
<212> TYPE: PRT
<213> ORGANISM: Homo sapiens

<400> SEQUENCE: 25

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 26
<211> LENGTH: 105
<212> TYPE: PRT
<213> ORGANISM: Homo sapiens

<400> SEQUENCE: 26

```
Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Thr Pro Ser Lys Gln Ser Asn Asn Lys
     50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105
```

<210> SEQ ID NO 27
<211> LENGTH: 330
<212> TYPE: PRT
<213> ORGANISM: Homo sapiens

<400> SEQUENCE: 27

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 29
<211> LENGTH: 330
<212> TYPE: PRT
<213> ORGANISM: Homo sapiens

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly

```
              210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 327
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 31
<211> LENGTH: 327
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Tyr
                20                  25                  30

Ile Glu Trp His Gln Gln Pro Glu Lys Gly Pro Arg Tyr Leu Met
            35                  40                  45

Lys Leu Asp Ser Asp Gly Ser His Ile Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Tyr Asp
                85                  90                  95

Ser Thr Ala Gly Ala Val Phe Gly Gly Gly Thr Gln Leu Thr Val Leu
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Gln His Ser Thr Tyr Tyr
                20                  25                  30

Ile Glu Trp Tyr Gln Gln Arg Pro Gly Arg Ser Pro Gln Tyr Ile Met
            35                  40                  45

Lys Leu Asp Ser Asp Gly Ser His Ile Lys Gly Asp Gly Ile Pro Asp
50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Val Tyr Asp
                85                  90                  95

Ser Thr Ala Gly Ala Val Phe Gly Gly Gly Thr Gln Leu Thr Val Leu
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 34

```
Gln Pro Val Leu Thr Gln Ser Ser Ala Ser Ala Ser Leu Gly Ser
1               5                   10                  15

Ser Val Lys Leu Thr Cys Thr Leu Ser Ser Gln His Ser Thr Tyr Tyr
            20                  25                  30

Ile Glu Trp His Gln Gln Pro Gly Lys Ala Pro Arg Tyr Leu Met
            35                  40                  45

Lys Leu Asp Ser Asp Gly Ser His Ile Lys Gly Asp Gly Val Pro Asp
    50                  55                  60

Arg Phe Ser Gly Ser Ser Ser Gly Ala Asp Arg Tyr Leu Thr Ile Ser
65                  70                  75                  80

Asn Leu Gln Leu Glu Asp Glu Ala Asp Tyr Tyr Cys Gly Val Tyr Asp
                85                  90                  95

Ser Thr Ala Gly Ala Val Phe Gly Gly Gly Thr Gln Leu Thr Val Leu
                100                 105                 110
```

<210> SEQ ID NO 35
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Gln Pro Val Leu Thr Gln Pro Pro Ser Ala Ser Ala Ser Leu Gly Ala
1               5                   10                  15

Ser Val Thr Leu Thr Cys Thr Leu Ser Ser Gln His Ser Thr Tyr Tyr
            20                  25                  30

Ile Glu Trp Tyr Gln Gln Arg Pro Gly Lys Gly Pro Arg Phe Val Met
            35                  40                  45

Arg Leu Asp Ser Asp Gly Ser His Ile Lys Gly Asp Gly Ile Pro Asp
    50                  55                  60

Arg Phe Ser Val Leu Gly Ser Gly Leu Asn Arg Tyr Leu Thr Ile Lys
65                  70                  75                  80

Asn Ile Gln Glu Glu Asp Glu Ser Asp Tyr His Cys Gly Val Tyr Asp
                85                  90                  95

Ser Thr Ala Gly Ala Val Phe Gly Gly Gly Thr Gln Leu Thr Val Leu
                100                 105                 110
```

<210> SEQ ID NO 36
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
            35                  40                  45

Trp Ile Gly Phe Leu Tyr Tyr Glu Gly Asp Thr Tyr Tyr Asn Pro Ser
    50                  55                  60
```

-continued

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 37
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Leu Gln Leu Gln Glu Ser Gly Ser Gly Leu Val Lys Pro Ser Gln
1               5                   10                  15

Thr Leu Ser Leu Thr Cys Ala Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 38
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln His Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

```
Gly Gln Gly Thr Leu Val Thr Val Ser Ser
        115                 120
```

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120
```

<210> SEQ ID NO 40
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln His Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120
```

<210> SEQ ID NO 41
<211> LENGTH: 122
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Ile Thr Thr Pro
            20                  25                  30

Asp Tyr Ser Trp His Trp Ile Arg Gln Pro Pro Gly Lys Ala Leu Glu
        35                  40                  45

Trp Leu Ala Phe Leu Tyr Tyr Glu Gly Asp Thr Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Ile Thr Thr Pro

```
                    20                  25                  30

Asp Tyr Ser Trp His Trp Ile Arg Gln Pro Pro Gly Lys Ala Leu Glu
            35                  40                  45

Trp Leu Ala Phe Leu Tyr Tyr Glu Gly Asp Thr Tyr Tyr Asn Pro Ser
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
            115                 120

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Tyr
            20                  25                  30

Ile Glu Trp His Gln Gln Pro Glu Lys Gly Pro Arg Tyr Leu Met
            35                  40                  45

Lys Val Asp Ser Asp Gly Ser His Ile Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Tyr Asp
                85                  90                  95

Ser Thr Ala Gly Ala Val Phe Gly Gly Gly Thr Gln Leu Thr Val Leu
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Pro Val Leu Thr Gln Ser Ser Ala Ser Ala Ser Leu Gly Ser
1               5                   10                  15

Ser Val Lys Leu Thr Cys Thr Leu Ser Ser Gln His Ser Thr Tyr Tyr
            20                  25                  30

Ile Glu Trp His Gln Gln Pro Gly Lys Ala Pro Arg Tyr Leu Met
            35                  40                  45

Lys Val Asp Ser Asp Gly Ser His Ile Lys Gly Asp Gly Val Pro Asp
        50                  55                  60

Arg Phe Ser Gly Ser Ser Ser Gly Ala Asp Arg Tyr Leu Thr Ile Ser
65                  70                  75                  80

Asn Leu Gln Leu Glu Asp Glu Ala Asp Tyr Tyr Cys Gly Val Tyr Asp
```

```
                    85                  90                  95

Ser Thr Ala Gly Ala Val Phe Gly Gly Gly Thr Gln Leu Thr Val Leu
                100                 105                 110

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Gln His Ser Thr Tyr Tyr
                20                  25                  30

Ile Glu Trp Tyr Gln Gln Arg Pro Gly Arg Ser Pro Gln Tyr Ile Met
            35                  40                  45

Lys Val Asp Ser Asp Gly Ser His Ile Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Val Tyr Asp
                85                  90                  95

Ser Thr Ala Gly Ala Val Phe Gly Gly Gly Thr Gln Leu Thr Val Leu
                100                 105                 110

<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gln His Ser Thr Tyr Tyr
                20                  25                  30

Ile Glu Trp Tyr Gln Gln Arg Pro Gly Lys Gly Pro Arg Phe Val Met
            35                  40                  45

Arg Val Asp Ser Asp Gly Ser His Ile Lys Gly Asp Gly Ile Pro Asp
    50                  55                  60

Arg Phe Ser Val Leu Gly Ser Gly Leu Asn Arg Tyr Leu Thr Ile Lys
65                  70                  75                  80

Asn Ile Gln Glu Glu Asp Glu Ser Asp Tyr His Cys Gly Val Tyr Asp
                85                  90                  95

Ser Thr Ala Gly Ala Val Phe Gly Gly Gly Thr Gln Leu Thr Val Leu
                100                 105                 110

<210> SEQ ID NO 48
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120
```

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Leu Gln Leu Gln Glu Ser Gly Ser Gly Leu Val Lys Pro Ser Gln
1               5                   10                  15

Thr Leu Ser Leu Thr Cys Ala Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120
```

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln His Pro Gly Lys Gly Leu Glu
        35                  40                  45
```

Trp Ile Gly Phe Leu Tyr Tyr Glu Gly Asp Thr Tyr Tyr Asn Pro Ser
            50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
            115                 120

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
            115                 120

<210> SEQ ID NO 52
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Thr Pro
            20                  25                  30

Asp Tyr Ser Trp His Trp Ile Arg Gln Pro Pro Gly Lys Gly Leu Glu
        35                  40                  45

Trp Ile Gly Phe Leu Tyr Tyr Glu Gly Asp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

```
Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 53
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Ile Thr Thr Pro
            20                  25                  30

Asp Tyr Ser Trp His Trp Ile Arg Gln Pro Pro Gly Lys Ala Leu Glu
        35                  40                  45

Trp Leu Ala Phe Leu Tyr Tyr Glu Gly Asp Thr Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 54
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Ile Thr Thr Pro
            20                  25                  30

Asp Tyr Ser Trp His Trp Ile Arg Gln Pro Pro Gly Lys Ala Leu Glu
        35                  40                  45

Trp Leu Ala Phe Leu Tyr Tyr Glu Gly Asp Thr Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Lys Tyr Ser Gly Tyr Gly Asn Trp Phe Ala Tyr Trp
            100                 105                 110

Gly Gln Gly Thr Leu Val Thr Val Ser Ser
        115                 120

<210> SEQ ID NO 55
```

-continued

<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Ser Ile Gly
            20                  25                  30

Pro Ile His Leu Met His Trp Tyr Gln Gln Lys Pro Gly Gln Pro Pro
        35                  40                  45

Lys Leu Leu Ile Tyr Gly Ala Ser Asn Pro Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Gly Lys
                85                  90                  95

Glu Ser Pro Arg Thr Phe Gly Gln Gly Thr Lys Leu Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Ser Ile Gly
            20                  25                  30

Pro Ile His Leu Met His Trp Tyr Gln Gln Lys Pro Gly Gln Pro Pro
        35                  40                  45

Lys Leu Leu Ile Tyr Gly Ala Ser Asn Pro Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Gly Lys
                85                  90                  95

Glu Ser Pro Arg Thr Phe Gly Pro Gly Thr Lys Val Asp Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Ser Ile Gly
            20                  25                  30

```
Pro Ile His Leu Met His Trp Tyr Gln Gln Lys Pro Gly Gln Ala Pro
            35                  40                  45

Arg Leu Leu Ile Tyr Gly Ala Ser Asn Pro Glu Ser Gly Ile Pro Ala
 50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Lys
                85                  90                  95

Glu Ser Pro Arg Thr Phe Gly Gln Gly Thr Lys Leu Glu Ile Lys
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ser Val Ser Ile Gly
            20                  25                  30

Pro Ile His Leu Met His Trp Tyr Gln Gln Lys Pro Gly Gln Ala Pro
            35                  40                  45

Arg Leu Leu Ile Tyr Gly Ala Ser Asn Pro Glu Ser Gly Ile Pro Asp
 50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Gly Lys
                85                  90                  95

Glu Ser Pro Arg Thr Phe Gly Gln Gly Thr Lys Leu Glu Ile Lys
            100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Ile Gly
            20                  25                  30

Pro Ile His Leu Met His Trp Tyr Gln Gln Lys Pro Gly Gln Ala Pro
            35                  40                  45

Arg Leu Leu Ile Tyr Gly Ala Ser Asn Pro Glu Ser Gly Ile Pro Ala
 50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Gly Lys
                85                  90                  95

Glu Ser Pro Arg Thr Phe Gly Gln Gly Thr Lys Leu Glu Ile Lys
            100                 105                 110
```

```
<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Ile Gly
            20                  25                  30

Pro Ile His Leu Met His Trp Tyr Gln Gln Lys Pro Gly Gln Pro Pro
        35                  40                  45

Lys Leu Leu Ile Tyr Gly Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Gly Lys
                85                  90                  95

Glu Ser Pro Arg Thr Phe Gly Gln Gly Thr Lys Leu Glu Ile Lys
            100                 105                 110

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Arg Ser Gly
            20                  25                  30

Tyr Trp Trp Ser Trp Ile Arg Gln His Pro Gly Lys Gly Leu Glu Trp
        35                  40                  45

Ile Gly Gln Ile Tyr Asn Lys Gly Asn Thr Asp Asn Asn Pro Ser Leu
    50                  55                  60

Lys Ser Leu Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Glu Ser Gly Pro Gly Leu Val Lys Pro Ser Glu
```

-continued

```
                1               5                  10                 15
Thr Leu Ser Leu Thr Cys Ala Val Ser Gly Tyr Ser Ile Arg Ser Gly
            20                  25                 30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
            115

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Pro Gly Leu Val Lys Pro Ser Glu
1               5                  10                 15

Thr Leu Ser Leu Thr Cys Thr Val Ser Gly Tyr Ser Ile Arg Ser Gly
            20                  25                 30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
            115

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Gln Glu Ser Gly Pro Gly Leu Val Lys Pro Pro Gly
1               5                  10                 15

Thr Leu Ser Leu Thr Cys Ala Val Ser Gly Tyr Ser Ile Arg Ser Gly
            20                  25                 30

Tyr Trp Trp Ser Trp Val Arg Gln Pro Pro Gly Lys Gly Leu Glu Trp
        35                  40                  45
```

```
Ile Gly Gln Ile Tyr Asn Lys Gly Asn Thr Asp Asn Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg Val Phe Trp Asp Asp Ala Tyr Phe Asp Val Trp Gly Gln Gly
                100                 105                 110

Thr Met Val Thr Val Ser Ser
        115

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
                20                  25                  30

Tyr Trp Trp Ser Trp Ile Arg Gln Pro Pro Gly Lys Gly Leu Glu Trp
                35                  40                  45

Ile Gly Gln Ile Tyr Asn Lys Gly Asn Thr Asp Asn Asn Pro Ser Leu
    50                  55                  60

Lys Ser Gln Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
                100                 105                 110

Thr Met Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
                20                  25                  30

Tyr Trp Trp Ser Trp Ile Arg Gln Pro Pro Gly Lys Gly Leu Glu Trp
                35                  40                  45

Ile Gly Gln Ile Tyr Asn Lys Gly Asn Thr Asp Asn Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Arg Ser Val Thr Ala Ala Glu Asp Thr Ala Val Tyr Tyr Cys
                85                  90                  95
```

```
Ala Arg Val Phe Trp Asp Asp Ala Tyr Phe Asp Val Trp Gly Gln Gly
            100                 105                 110

Thr Met Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
            20                  25                  30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Asn Pro Ser Leu
    50                  55                  60

Lys Ser Gln Val Thr Ile Ser Val Asp Thr Ser Lys Asn Gln Phe Ser
65                  70                  75                  80

Leu Lys Leu Arg Ser Val Thr Ala Glu Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
            20                  25                  30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Asn Pro Ala Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115
```

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
            20                  25                  30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Ser Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115
```

<210> SEQ ID NO 70
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Arg Ser Gly
            20                  25                  30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Pro Ala Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115
```

<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Arg Ser Gly
            20                  25                  30

Tyr Trp Trp Ser Trp Ile Arg Gln Pro Pro Gly Lys Gly Leu Glu Trp
        35                  40                  45

Ile Gly Gln Ile Tyr Asn Lys Gly Asn Thr Asp Asn Ser Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115

<210> SEQ ID NO 72
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
            20                  25                  30

Tyr Trp Trp Ser Trp Ile Arg Gln Pro Gly Lys Gly Leu Glu Trp
        35                  40                  45

Ile Gly Gln Ile Tyr Asn Lys Gly Asn Thr Asp Asn Pro Ala Leu
    50                  55                  60

Lys Ser Gln Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Asp Ala Tyr Phe Asp Val Trp Gly Gln Gly
            100                 105                 110

Thr Met Val Thr Val Ser Ser
        115

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Arg Ser Gly
            20                  25                  30

```
Tyr Trp Trp Ser Trp Ile Arg Gln Gln Pro Gly Lys Gly Leu Glu Trp
            35                  40                  45

Ile Gly Gln Ile Tyr Asn Lys Gly Asn Thr Asp Asn Ser Pro Ser Leu
    50                  55                  60

Lys Ser Gln Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Phe Trp Asp Ala Tyr Phe Asp Val Trp Gly Gln Gly
            100                 105                 110

Thr Met Val Thr Val Ser Ser
        115

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ile Tyr Asn Lys Gly Asn Thr Asp Asn Asn Pro Ala Leu Lys Ser
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ile Tyr Asn Lys Gly Asn Thr Asp Asn Ser Pro Ser Leu Lys Ser
1               5                   10                  15
```